United States Patent

Hamilton et al.

Patent Number: 5,275,056
Date of Patent: Jan. 4, 1994

[54] GYRATORY SHEAR MATERIAL COMPACTING DEVICE

[75] Inventors: Edward R. Hamilton; Raymond D. Alexander; Lawrence E. Hart, all of Austin, Tex.

[73] Assignee: Rainhart Co., Austin, Tex.

[21] Appl. No.: 963,541

[22] Filed: Oct. 20, 1992

[51] Int. Cl.⁵ .............................................. G01N 3/56
[52] U.S. Cl. ...................................... 73/794; 425/169; 425/411; 425/415; 425/421
[58] Field of Search ................... 73/794, 795; 425/169, 425/171, 409, 411, 415, 419, 421, 429

[56] References Cited

U.S. PATENT DOCUMENTS

| | | | |
|---|---|---|---|
| 2,972,249 | 2/1961 | McRae et al. | 366/56 |
| 3,461,717 | 8/1969 | Dunlap et al. | 73/84 |
| 3,478,572 | 11/1969 | McRae et al. | 73/9 |
| 3,814,788 | 6/1974 | Livera | 425/419 |
| 4,942,768 | 7/1990 | McRae | 73/795 |
| 5,036,709 | 8/1991 | McRae | 73/841 |

FOREIGN PATENT DOCUMENTS 1633328  3/1991  U.S.S.R. ............................ 73/794

OTHER PUBLICATIONS

Bonnot, "Evaluation Methods for Properties of Bituminous Mixtures", Public Works Nat'l Research Lab., Paris, France 1986; Session #135; pp. 1-6.
"Method of Compacting Test Specimens of Bituminous Mixtures", Texas State Dept. of Hwys. and Public Transportation; Mar. 1991 Rev.; Parts I-II.
Moutier, "La Presse a Cisaillement Giratoire Modele de Serie", Bull Liaison Labo. P. et Ch. 74, Nov.-Dec. 1974; pp. 137-148.
Rainhart Cat. No. 140, "Gyratory Shear Molding Press" p. 31.
MAP Publication, "Gyratory Shear Compacting Press" 3 pgs.

Primary Examiner—Jay H. Woo
Assistant Examiner—James P. Mackey
Attorney, Agent, or Firm—Jones, Tullar & Cooper

[57] ABSTRACT

A gyratory shear material compacting device in which a material sample is placed within a cylindrical mold having a wobble plate. The material sample is compressed by a piston while the mold is simultaneously gyrated. Gyration is achieved by tilting the mold and holding the wobble plate within rollers which revolve around the mold, controlling the selected angle of tilt while imparting oscillatory gyration. The selected angle of tilt of the mold may be precisely controlled at all times, preventing the mold from riding up on the sample, or from coming into contact with the base of the device. The mold is free to advance rotationally. The device is capable of measuring and recording the height of the sample, angle of gyration, and moment of gyration.

20 Claims, 3 Drawing Sheets

GYRATORY SHEAR MATERIAL COMPACTING DEVICE

FIELD OF THE INVENTION

The present invention is directed generally to a gyratory shear material compacting device. More particularly, the present invention is directed to a gyratory shear material compacting and densification device. Most specifically, the present invention is directed to a gyratory shear material compacting device for producing a laboratory sample of a material, such as asphalt, bitumen, soil, or similar substance, by gyratory compaction and densification of a material sample so that the material sample's properties approximate those of the material during construction, under actual use, and with time.

DESCRIPTION OF THE PRIOR ART

In the construction of vehicular traveled structures such as roads, parking lots, runways, and similar structures, loose construction materials such as asphalt or soil are compacted to achieve greater strength and wearability. These loose construction materials are compacted more efficiently if an element of lateral shear is included along with the vertical compacting stress. During the construction of vehicular traveled structures, this combination of vertical stress and lateral shear is achieved by kneading, such as through the use of a sheeps-foot roller, or by rolling, such as by use of multiple wheels side-by-side on a common axis.

Once a vehicular traveled structure has been completed and put into use, the construction material remains somewhat flexible. When a vehicle travels over the structure, the structure will deflect and then rebound as the wheels of the vehicle pass. This deflection is not purely compressive, but also has a lateral shear component as the internal particles move away from the load of the wheel, and then back after the wheel has passed.

For testing purposes, it is necessary to obtain laboratory samples of compacted construction materials to ensure that construction materials meet required construction specifications, to simulate the material under vehicular traffic, and the like. These laboratory samples should be representative of the condition of the construction material as it exists in the actual vehicular traveled structure. A device for creating such samples should be capable of imparting both a compressive stress and a lateral shear, and also be capable of controllably varying both parameters.

Devices for compacting laboratory samples are known in the prior art. In some of these prior devices the sample is subjected to pure compressive forces alone, such as by compressing the sample within a cylinder. These devices do not create samples representative of the condition of the material in an actual vehicular traveled structure since there is little lateral shear strain imparted to the sample.

In other prior art devices there are included a pair of opposed plungers for compressing construction materials within a removable cylindrical mold. The construction material is placed in the mold, the mold is placed in a mold chuck, and the mold chuck is then mounted for gyratory oscillatory motion about the axis of the plungers. This is achieved by tilting the mold chuck relative to the axis of the plungers, and gyrating the mold chuck while under axial compressive stress. The tilt and gyration of the mold create a wobbling effect which imparts a lateral shear strain to the sample, while at the same time subjecting the sample to a compressive stress.

In these devices, when the mold is mounted in the mold chuck, and the mold chuck is mounted in the compaction device, the mold chuck and the mold are restrained from rotational movement during gyration. This can create a torsional force on the sample, counter to the natural seating direction of the sample. The effect of this torsional force adds an unknown parameter to the treatment of the sample, and may produce effects which cannot be determined.

There is, however, known in the prior art a compacting device that does not require a mold chuck, and allows the mold to rotate freely with the sample. In this device the mold includes a wobble plate which is mounted at an angle or tilt between rollers. The rollers revolve around the mold creating an oscillatory gyration action while a piston compresses the sample. Since the mold is free to rotate, there is no torsional force imparted to the sample. However, in this device the mold is tilted at a fixed angle during gyration, and there is no provision for varying the angle of tilt while gyration is being performed. In addition, there is no provision for measuring the force required to tilt the mold during gyration (the moment of gyration) nor is there a provision for measuring the change in the moment of gyration as the mold is gyrated. Furthermore, this prior device had no provision for holding the moment of gyration constant while allowing the angle of tilt of the mold to vary during gyration, nor was there a provision for measuring the change in the angle of tilt.

It will be apparent that a need exists for a gyratory shear material compacting device which overcomes the limitations of the prior art devices. The gyratory shear material compacting device in accordance with the present invention overcomes these limitations of the prior devices and provides a significant advance in the art.

SUMMARY OF THE INVENTION

It is an object of the present invention to provide a gyratory shear material compacting device.

Another object of the present invention is to provide a gyratory shear material compacting device for imparting gyratory shear compaction to a laboratory sample of a material.

A further object of the present invention is to provide a gyratory shear material compacting device capable of imparting a controllable compressive stress and a controllable lateral shear to a sample of material without imparting a torsional force on the sample.

An additional object of the present invention is to provide a gyratory shear material compacting device that does not require the use of a mold chuck, and which also gives variable and measurable control over the angle of tilt.

Yet another object of the present invention is to provide a gyratory shear material compacting device in which the mold containing the material sample is free to rotationally advance or turn in the natural seating direction of the sample as the mold is gyrated, while the mold is held at a constant tilt angle and the moment of gyration is measured.

An additional object of the present invention is to provide a gyratory shear material compacting device in which the mold is free to rotationally advance while the moment of gyration may be held constant during gyration, and the change in the angle of tilt may be measured.

Still a further object of the present invention is to provide a gyratory shear material compacting device which will create laboratory samples of materials that are representative of the materials in actual use.

As will be discussed in detail in the description of the preferred embodiment which is set forth subsequently, the gyratory shear material compacting device in accordance with the present invention utilizes a mold which does not require a mold chuck for mounting in a compaction device. The present invention includes movable upper and lower rollers for providing gyration. The mold of the present invention is provided with a coaxial wobble plate by which the mold may be gyrated when the wobble plate is mounted within the rollers. Since the mold is not mounted within a mold chuck, the mold is free to advance rotationally. The position of the rollers, and thereby the angle of tilt of the mold may be precisely controlled and adjusted, and the moment of gyration may be measured against other variables. In addition, the moment of gyration may be held constant while the change in the angle of tilt is measured against other variables.

The gyratory shear material compacting device in accordance with the present invention overcomes the limitations of the prior art devices and provides an assembly which creates samples under precisely known and controllable parameters. The gyratory shear material compacting device provides a substantial advance in the art.

BRIEF DESCRIPTION OF THE DRAWINGS

While the novel features of the gyratory shear material compacting device in accordance with the present invention are set forth with particularity in the appended claims, a full and complete understanding of the invention may be had by referring to the detailed description of the preferred embodiment which is set forth subsequently, and as illustrated in the accompanying drawings in which:

DESCRIPTION OF THE PREFERRED EMBODIMENT

Figure 1:
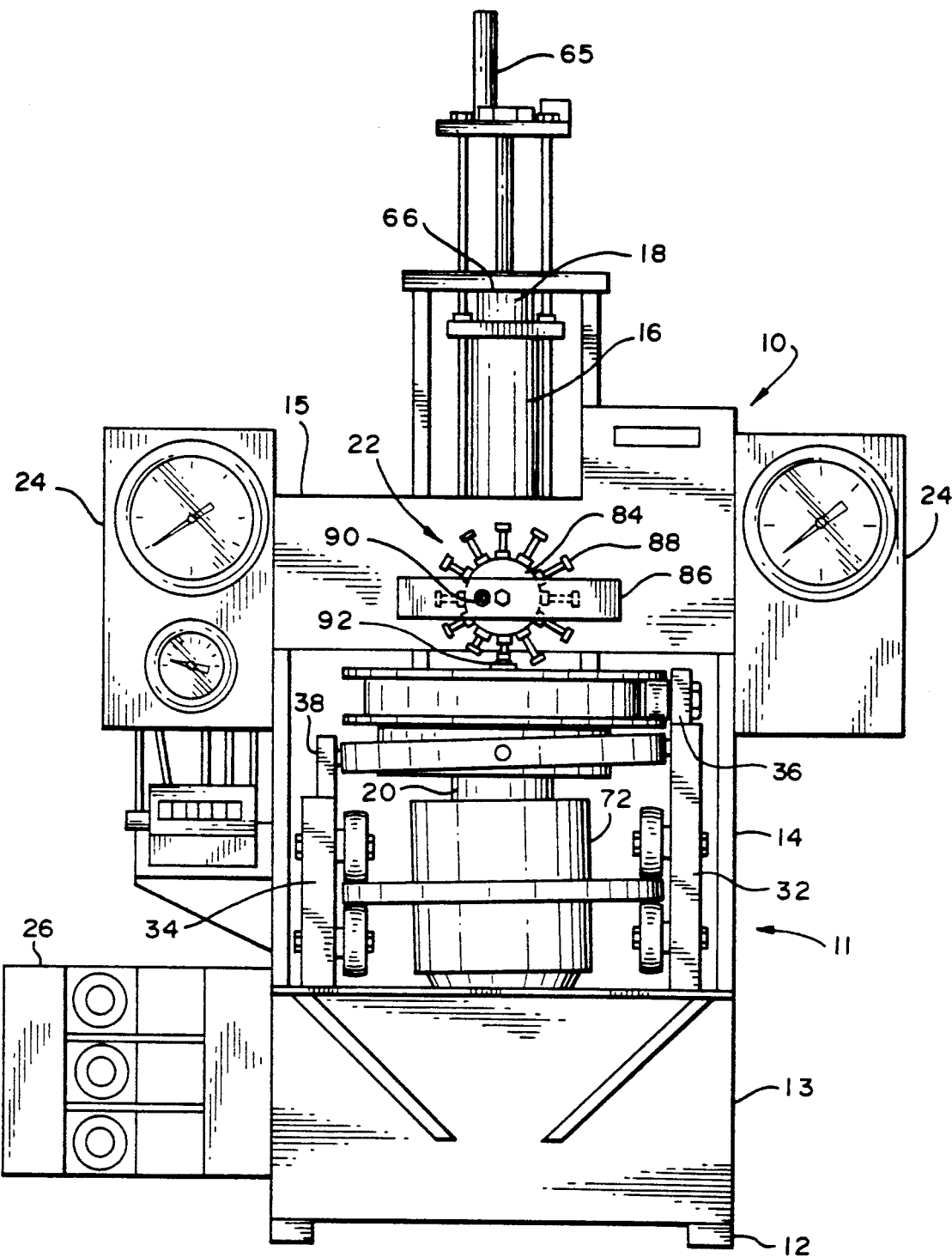
FIG. 1 is a front view of a gyratory shear material compacting device in accordance with the present invention.

Referring initially to FIG. 1, there may be seen generally at 10 a front view of a preferred embodiment of a gyratory shear material compacting device in accordance with the present invention. Compacting device 10 rests on a base 12 which supports a frame 11. Frame 11 consists of a bottom structure 13, side structures 14, and a top structure 15. Top structure 15 supports a vertical cylinder 16, which contains an upper tilt piston 18, and a lower main piston 20, each independently movable in opposite directions within the cylinder. Mounted on frame 11 is a turret 22, for controlling the height of movement of tilt piston 18. Also mounted on frame 11 are various gauges 24, and control instrumentation 26.

Figure 2:
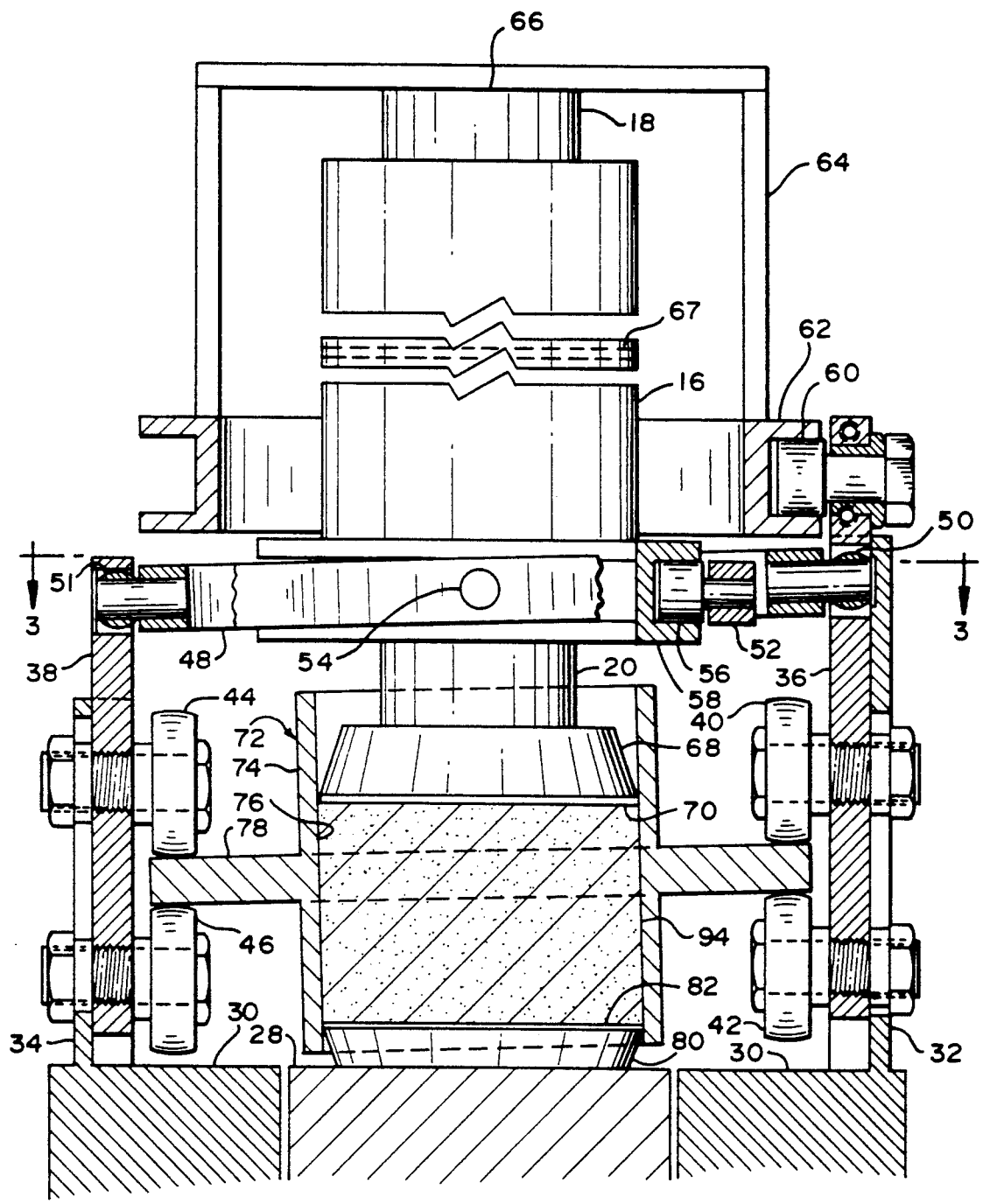
FIG. 2 is an enlarged detail of a portion of the device shown in FIG. 1, partially in section.

Turning now to FIG. 2, there is shown a circular fixed base platen 28 in the annulus of a circular turntable 30, both being supported by bottom structure 13 (FIG. 1). Turntable 30 has a driving means (not shown) for rotating turntable 30 about base platen 28 in a horizontal plane. The speed at which turntable 30 is rotated may be controllably varied to produce different or variable rates of gyration.

Fixed to turntable 30, extending vertically upwards therefrom, and opposed to one another are a major vertical track 32, and a minor vertical track 34, each having a C-shaped cross section. Mounted within major vertical track 32 is an elongated major slide 36, having a rectangular cross section. Major slide 36 is mounted within major vertical track 32 such that major slide 36 may slide up and down in the vertical direction, but is restrained in the other directions. Mounted within minor vertical track 34 is an elongated minor slide 38, having a rectangular cross section. Minor slide 38 is mounted within minor vertical track 34 such that minor slide 38 may slide up and down in the vertical direction, but is restrained in the other directions.

Fixed on the inboard side of major slide 36 are an upper major roller 40, and a lower major roller 42. Fixed on the inboard side of minor slide 38 are an upper minor roller 44, and a lower minor roller 46. Disposed between major slide 36 and minor slide 38 is an outer ring 48, Concentric with cylinder 16. Outer ring 48 is connected to the upper end of major slide 36 by major slide ball joint 50, and the upper end of minor slide 38 by minor slide ball joint 51, concentric with cylinder 16.

Figure 3:
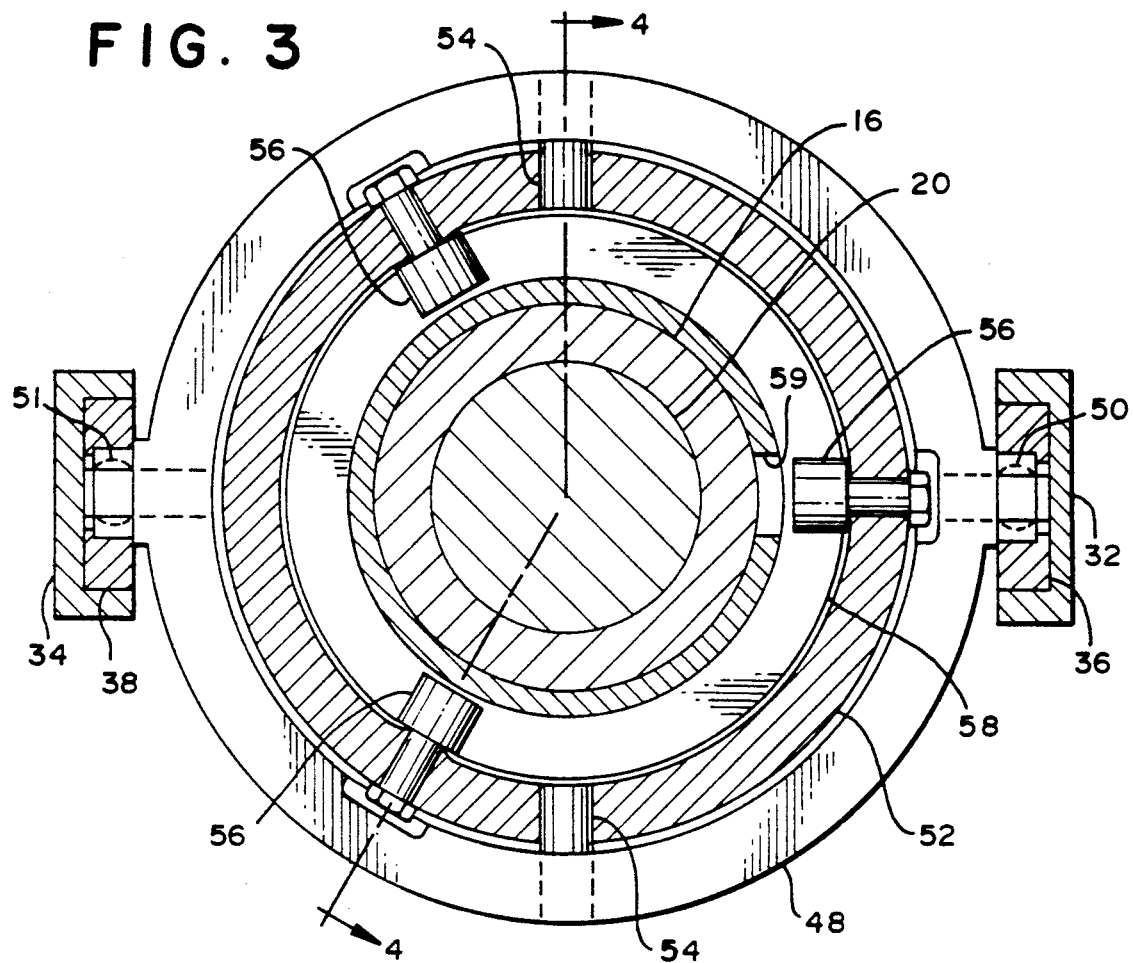
FIG. 3 is a cross-sectional view of FIG. 2 taken through line 3—3.

Outer ring 48 has concentrically disposed within its annulus a middle ring 52. Outer ring 48 is pivotably connected to middle ring 52 by a pair of pivot pins 54, as may be seen more clearly in FIG. 3. A circular lower track 58 having a C-shaped cross section is concentrically disposed within the annulus of middle ring 52. Three lower track cam followers 56 are mounted on the inner side of middle ring 52 and support middle ring 52 rollably within circular lower track 58. Assembly opening 59 in the vertical wall of circular lower track 58 permits lower track ca followers 56 to be assembled on middle ring 52 within circular lower track 58.

Figure 4:
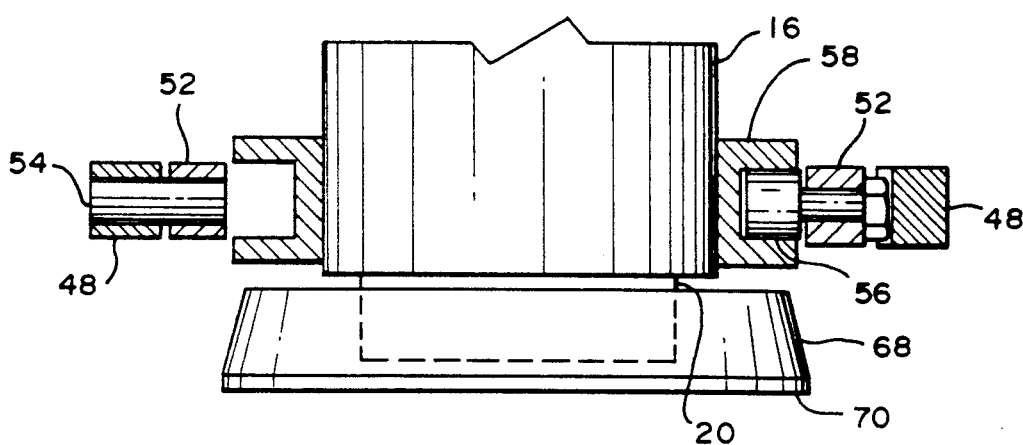
FIG. 4 is a cross-sectional view of FIG. 3 taken through line 4—4.

As may be seen more clearly by referring to FIG. 4, circular lower track 58 is fixed concentrically around cylinder 16. Lower track cam followers 56 are disposed in circular lower track 58 such that middle ring 52 is fixed in the horizontal plane by the flanges of circular lower track 58, and able to rotate freely about the vertical axis of cylinder 16. Since pivot pins 54 are fixed in middle ring 52, the pivot point of outer ring 48 remains at all times in the same horizontal plane as middle ring 52, and is likewise able to rotate about the vertical axis of cylinder 16 in the same horizontal plane as middle ring 52.

Referring back to FIG. 2, a circular upper track 62 having a C-shaped cross section is mounted concentrically with cylinder 16, movable up and down in the vertical direction. Mounted on the upper end of major slide 36, above major slide ball joint 50 is an upper track cam follower 60 which extends inward, and rides within circular upper track 62. Circular upper track 62 is supported by a tilt piston bridge 64 which is mounted upon tilt piston 18. A linear transducer 65 (FIG. 1) is mounted above tilt piston bridge 64 such that it may measure changes in the altitude of tilt piston 18. The altitude of circular upper track 62 changes as the altitude of tilt piston 18 is changed. This change in altitude changes the angle of tilt a calculatable amount. Thus, transducer 65 may be used to measure changes in the angle tilt.

A force measuring means 66 is mounted between tilt piston 18 and tilt piston bridge 64 for measuring the force required to maintain a selected angle of tilt, this force times the constant distance from the center line of gyration being the moment of gyration. The greater the moment of gyration, the greater the load on tilt piston 18.

A diaphragm 67 within cylinder 16 separates tilt piston 18 from main piston 20 such that they may be independently controlled and activated. A main piston head 68 is disposed on the lower end of main piston 20, and has piston face 70. An additional linear transducer (not shown) is placed internal to the main piston to measure the relative position of the main piston, and for measuring the change in height of the sample during compression.

A mold 72 has a cylindrical mold body 74, having a bore 76 of greater diameter than piston face 70. Main piston head 68 is shaped so as to permit a close fit within bore 76 to prevent loss of material being compacted, but shaped so as to also permit angular movement of mold 72 with respect to the axis of cylinder 16. Main piston head 68 is insertable into bore 76 of mold 72, for retaining mold 72 from lateral movement.

Mounted approximately halfway up, and extending radially outward from the outside of mold body 74 is a circular wobble plate 78 generally disposed coaxially in a horizontal plane perpendicular to the axis of bore 76. Mold 72 is insertable into compacting device 10 such that the outer edge of wobble plate 78 fits between upper major roller 40 and lower major roller 42 on one edge, and between upper minor roller 44 and lower minor roller 46 on the opposite edge. The clearance between the upper and lower rollers 40, 42, 44, 46 and wobble plate 78 is such that the rollers may roll freely around the edge of wobble plate 78, while still closely retaining mold 7 at the selected angle of tilt. Each roller has a crowned or curved face, allowing close clearance when wobble plate 78 is level or only at a moderate tilt, but also allowing wobble plate 78 to be tilted at greater angles without binding.

A bottom mold plate 80, having a bottom plate face 82 is insertable into bore 76 of mold 72 opposite to main piston head 68. Bottom mold plate 80 rests loosely on base platen 28, when within mold 72, and is shaped so as to permit a close fit within bore 76 to prevent loss of material being compacted, but also shaped so as to permit angular movement of mold 7 with respect to the axis of cylinder 16.

Referring back to FIG. 1, Turret 22 has circular plate 84 mounted rotatably within a bracket 86 on top structure 15. A plurality of stop screws 88 of successively greater length extend radially from circular plate 84. Turret 22 may be indexed in place by a ball detent 90 mounted in bracket 86 such that one of the stop screws 88 is extended downward. The altitude of circular upper track 62 is limited by contact with the stop screw 88 extending downward from turret 22. A solid tab 92 extends inward from circular upper track 62 for contacting the stop screw 88 extending downward from turret 22, and to provide clearance between circular upper track 62 and the other stop screws 88 on turret 22. The altitude of circular upper track 62 may be decreased or increased by turning turret 22 such that a stop screw 88 of greater or lesser length is extending downward, and adjusting tilt piston 18 until solid tab 92 contacts the stop screw 88 extending downward. Circular plate 84 may be marked to indicate which stop screw position will yield what angle of tilt to mold 72.

In operation, to create a laboratory sample, mold 72, with bottom mold plate 80 in its bore, is filled with a known amount of a material sample 94. Mold 72 is then inserted into compacting device 10 by sliding the edges of wobble plate 78 between the upper and lower major and minor rollers, 40, 42, 44, 46, as shown in FIG. 2, except that the axis of bore 76 is normally vertical at this point, in-line with the axis of cylinder 16. Main piston head 68 is then extended into bore 76 of mold 72 by activating main piston 20 within cylinder 16. In the preferred embodiment, main piston 20, and tilt piston 18 are operable by a hydraulic system (not shown), but any suitable actuator may be used.

Main piston head 68 may be extended until main piston face 70 comes into contact with material sample 94, and any desired pressure may be continuously applied to material sample 94. The edge of main piston head 68 keeps mold 72 captive laterally, while the bottom mold plate 80 is kept captive laterally within the bore 76 of mold 72. A film of oil may be placed between the loose bottom mold plate 80 and the base platen 28.

To induce the desired tilt to mold 72, turret 22 is adjusted to the desired position and tilt piston 18 is activated. As tilt piston 18 rises, tilt piston bridge 64, circular upper track 62, and major slide 36 are raised with it to the desired altitude. Turret 22 prevents circular upper track 62 from rising above a predetermined altitude, stopping the upward movement of tilt piston 18. The raising of major slide 36 raises major slide ball joint 50 which causes outer ring 48 to pivot about pivot pins 54. This pivot action lowers minor slide ball joint 51, lowering minor slide 38. Since the major slide rollers 40, 42 are now disposed at a predetermined altitude greater than the minor slide rollers 44, 46, with wobble plate 78 inserted within them, mold 72 is tilted at a known angle at the predetermined altitude.

Pivot pins 54 in outer ring 48 are disposed opposite to one another at the centerline of cylinder 16 in the preferred embodiment. This creates a one-to-one ratio in which, as major slide 36 is raised a certain distance, minor slide 38 is lowered the same distance, thereby simplifying the force application as the moment of gyration, with the upward force on one side being equal to the downward force on the other side. In an alternative embodiment, (not shown) the pivot line of outer ring 48 could be off center from the centerline of cylinder 16, along a chord of outer ring 48. This would enable a different raise/lower ratio between major slide 36 and minor slide 38.

Once the desired tilt angle has been imposed upon the mold, turntable 30 may be activated at a desired speed. As turntable 30 revolves about base platen 28, major vertical track 32 and minor vertical track 34, being rigidly attached to turntable 30, revolve around mold 72, carrying with them major slide 36 and minor slide 38. As slides 36, 38 revolve around mold 72, lower major roller 42 raises one side of wobble plate 78, while upper minor roller 44 simultaneously depresses the other side of wobble plate 78, causing mold 72 to undergo an oscillatory gyrating action, imparting a lateral shear on material sample 94. Upper major roller 40 and lower minor roller 46 prevent the mold from deviating from the desired angle of tilt. Since mold 72 is at all times held within the rollers, mold 72 cannot ride up on the sample, nor come into contact with base platen 28.

The angle of tilt is known, controlled, and may be held constant at all times during the gyration process, while the mold is still free to advance rotationally with the seating direction of material sample 94.

As material sample 94 compresses and is gyrated, it will tend to want to straighten out the angle of tilt. Since the mold is held at the desired tilt angle, a force known as the moment of gyration is created, which will increase the load on the tilt mechanism. Force measuring means 66 may be used to measure and record this changing force as a function of another variable such as time, number of gyrations, or the like.

Alternatively, for some testing purposes it is desirable to hold the moment of gyration constant and allow mold 72 to straighten up as material sample 94 is compacted. The moment of gyration may be held constant by maintaining a constant pressure in tilt piston 18, while allowing tilt piston 18 to float as mold 72 is gyrated. As material sample 94 is compacted and gyrated, mold 72 will tend to straighten up, and the tilt angle will approach zero. The change in the tilt angle may be measured by transducer 65, and recorded as a function of another variable such as time, the number of gyrations, or the like.

To apply a constant moment of gyration, mold 72 is loaded into compacting device 10 in the same manner described above, and placed in compression by activating main piston 16 to the desired pressure. Tilt piston 18 is then raised under a constant hydraulic pressure, tilting mold 72 at some measurable angle. Turntable 30 may then be activated while the constant pressure in tilt piston 18 is maintained, resulting in the application of a constant moment of gyration on mold 72. As material sample 94 is compacted during successive gyrations, the tilt angle will tend to decrease and mold 72 will approach vertical, while transducer 65 may be used to record the changing tilt angle.

Following compaction of material sample 94, if it is desirable to square the sample, tilt piston 18 may be lowered until major slide 36 and minor slide 38 are level. Turntable 30 may be rotating during this squaring and for several revolutions thereafter with the load from main piston head 68 still applied.

While a preferred embodiment of a gyratory shear material compacting device in accordance with the present invention has been set forth fully and completely hereinabove, it will be apparent to one of skill in the art that a number of changes could be made without departing from the scope of the present invention. For example, while in the preferred embodiment bottom mold plate 80 is totally free to move on the plane of base platen 28, and main piston head 68 is fixed on main piston 20, three other combinations are also possible: (1) bottom mold plate 80 totally free to move on the plane of base platen 28, and main piston head 68 attached to main piston 20 such that m in piston head 68 may turn on the axis of main piston 20; (2) bottom mold plate 80 totally fixed on base platen 28, and main piston head 68 totally free to move on the plane at the end of main piston 20; and (3) bottom mold plate 80 fixed on base platen 28, but free to rotate about the axis of main piston 20, and main piston head 68 totally free to move on the plane at the end of main piston 20. Also, main piston 20 and base platen 28 can be reversed in position upper and lower, or two pistons could be used.

In addition, other changes in, for example the sizes of the cylinders, the specific type of drive means, the amount of vertical stress, the type, mass, and temperature of materials being compacted, and the like can be made without departing from the true spirit and scope of the present invention which is accordingly to be limited only by the following claims.

What is claimed is:

1. A gyratory shear material compacting device comprising:
   a mold for receiving a material;
   a frame supporting a compressing means for compressing said material within said mold;
   means for tilting said mold by applying moment forces approximately equally to opposite sides of said mold, said means for tilting said mold including means for applying a constant moment of gyration to said mold; and
   means for imparting an oscillatory gyration to said mold while said mold is free to advance rotationally.

2. The gyratory shear material compacting device of claim 1 wherein said mold includes an open-ended mold body, said mold body having a wobble plate mounted thereon.

3. The gyratory shear material compacting device of claim 1 further including means for measuring a change in the height of said material.

4. The gyratory shear material compacting device of claim 1 wherein said means for applying a constant moment of gyration includes a hydraulic cylinder maintaining a piston at a constant pressure while said piston remains movable within said cylinder.

5. The gyratory shear material compacting device of claim 1 further including a means for measuring a moment of gyration applied to said mold.

6. The gyratory shear material compacting device of claim 1 further including a means for measuring the angle at which said mold is tiled.

7. The gyratory shear material compacting device of claim 1 wherein said means for tilting said mold includes an elongated major vertical track having a major slide slidably disposed therein, and a minor vertical track having a minor slide slidably disposed therein, and wherein said mold includes an open-ended mold body having a wobble plate mounted thereon, and wherein said major slide and said minor slide each have a restraining means for receiving said wobble plate of said mold such that said restraining means may pass along the edge of said wobble plate.

8. The gyratory shear material compacting device of claim 7 wherein said means for tiling said mold includes:
   an outer ring swivably attached to said major slide on one side, and swivably connected to the upper end of said minor slide on the opposite side, and having a pivot point disposed there between;
   a middle ring for holding said pivot point at a fixed altitude, said middle ring and said outer ring being rotatable by rollable connection between said middle ring and a lower circular track.

9. A gyratory shear material compacting device comprising:
   a frame supporting a fixed compressing member and a movable compressing member opposed to said fixed compressing member;
   an actuating means for moving said movable compressing member toward said fixed compressing member;
   a mold having a mold body for receiving a material, said mold body having a wobble plate mounted thereon;

means associated with said compressing members for retaining said material within said mold;

means for tilting said mold by applying moment forces approximately equally to opposite sides of said wobble plate, said means for tilting said mold including means for applying a constant moment of gyration to said mold; and means for imparting an oscillatory gyration to said mold while said material in said old is maintained under compression, and while said mold is subject to said constant moment of gyration, said mold being free to advance rotationally.

10. The gyratory shear material compacting device of claim 9 wherein said means for retaining said material within said mold are free to rotate with said material.

11. The gyratory shear material compacting device of claim 9 further including a means for measuring a change in the height of said material.

12. The gyratory shear material compacting device of claim 9 wherein said means for applying a constant moment of gyration includes a hydraulic cylinder maintaining a piston at a constant pressure while said piston remains movable within said cylinder.

13. The gyratory shear material compacting device of claim 9 further including a means for measuring a moment of gyration applied to said mold.

14. The gyratory shear material compacting device of claim 9 further including a means for measuring the angle at which said mold is tilted.

15. The gyratory shear material compacting device of claim 9 wherein said means for tilting said mold includes an elongated major vertical track having a major slide slidably disposed therein, and a minor vertical track having a minor slide slidably disposed therein, and wherein said major slide and said minor slide each have a restraining means for receiving said wobble plate of said mold such that said restraining means may pass along the edge of said wobble plate, imparting gyration to said mold.

16. The gyratory shear material compacting device of claim 15 wherein said means for tilting said mold includes:

an outer ring swivably attached to said major slide on one side, and swivably connected to the upper end of said minor slide on the opposite side, and having a pivot point disposed there between;

a middle ring for holding said pivot point at a fixed altitude, said middle ring and said outer ring being rotatable about said movable compressing member by rollable connection between said middle ring and a lower circular track fixed to said movable compressing member.

17. A gyratory shear material compacting device comprising:

a frame supporting a turntable, said turntable having an annulus;

a fixed compressing means situated within said annulus, said turntable being rotatable about said fixed compressing means;

a major vertical track fixed to said turntable and extending from said turntable, said major vertical track having a major slide slidably mounted therein;

a minor vertical track fixed to said turntable and extending from said turntable, said minor vertical track having a minor slide slidably mounted therein;

a mold having a mold body with a bore capable of receiving a material, said mold having a wobble plate mounted on said mold body and extending outward therefrom;

a movable compressing means mounted on said frame opposite from said fixed compressing means, said movable compressing means having a material contacting means insertable within the bore of said mold;

a material contacting means associated with said fixed compressing means, insertable within the bore of said mold;

a restraining means mounted on said major slide and said minor slide for receiving said wobble plate of said mold such that said restraining means may pass along the edge of said wobble plate; and means for adjusting the altitudes of said major slide and said minor slide such that a tilt angle may be imparted to said mold when said mold is disposed within said restraining means;

whereby driving said turntable drives said major slide and said minor slide around said mold, said restraining means lifting one edge of said wobble plate and lowering the opposite edge of said wobble plate, causing an oscillatory gyration of said mold to occur, and said mold being free to advance rotationally.

18. The gyratory shear material compacting device of claim 17 wherein said means for adjusting the altitudes of said major slide and said minor slide includes a means for applying a constant moment of gyration to said mold.

19. The gyratory shear material compacting device of claim 18 wherein said means for applying a constant moment of gyration to said mold includes a hydraulic cylinder having a piston disposed therein and maintained under a constant pressure.

20. The gyratory shear material compacting device of claim 17 wherein said means for adjusting the altitudes of said major slide and said minor slide includes an outer ring swivably connected to said major slide and said minor slide, said outer ring having a pivot point held at a fixed altitude by a middle ring, said middle ring and said outer ring being rotatable about said movable compressing means by rollable connection between said middle ring and a lower circular track fixed to said movable compressing means.

* * * * *